(12) United States Patent
Fujimori et al.

(10) Patent No.: US 10,677,769 B2
(45) Date of Patent: Jun. 9, 2020

(54) PRODUCTIVITY EVALUATION METHOD, PRODUCTIVITY EVALUATION DEVICE, PROGRAM, AND RECORDING MEDIUM

(71) Applicant: SEKISUI CHEMICAL CO., LTD., Osaka (JP)

(72) Inventors: Yoji Fujimori, Kumagaya (JP); Akio Shokaku, Tsukuba (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 15/671,598

(22) Filed: Aug. 8, 2017

(65) Prior Publication Data
US 2017/0336376 A1 Nov. 23, 2017

Related U.S. Application Data

(63) Continuation of application No. 14/423,246, filed as application No. PCT/JP2013/075292 on Sep. 19, 2013, now abandoned.

(30) Foreign Application Priority Data

Sep. 20, 2012 (JP) ................................. 2012-206979

(51) Int. Cl.
*G01N 33/00* (2006.01)
*G06Q 50/04* (2012.01)
(Continued)

(52) U.S. Cl.
CPC ....... *G01N 33/0036* (2013.01); *C07C 29/151* (2013.01); *G01N 31/10* (2013.01);
(Continued)

(58) Field of Classification Search
CPC .. G01N 33/0036; G01N 31/10; C07C 29/151; G06Q 50/04; Y10T 436/204165
See application file for complete search history.

(56) References Cited

U.S. PATENT DOCUMENTS

2007/0275447 A1* 11/2007 Lewis ................. C12P 7/06
435/161

FOREIGN PATENT DOCUMENTS

JP        6-325052      11/1994
JP        2005-87987     4/2005
(Continued)

OTHER PUBLICATIONS

Huber, George W., Sara Iborra, and Avelino Corma. "Synthesis of transportation fuels from biomass: chemistry, catalysts, and engineering." Chemical reviews 106.9 (2006): 4044-4098.*

(Continued)

*Primary Examiner* — Robert J Eom
(74) *Attorney, Agent, or Firm* — Wenderoth, Lind & Ponack, L.L.P.

(57) ABSTRACT

This productivity evaluation method is for evaluating productivity of a chemical substance in a process comprising a first step of obtaining gas from a waste material and a second step of synthesizing a chemical substance from the gas obtained in the first step in the presence of a catalyst, said method including: a first carbon mass calculation stage of calculating mass of carbon contained in the waste material, a second carbon mass calculation stage of calculating mass of carbon contained in the chemical substance produced in said process, and a productivity evaluation stage of evaluating the productivity of the chemical substance based on values of the mass of carbon which are calculated in the first carbon mass calculation stage and the second carbon mass calculation stage.

9 Claims, 5 Drawing Sheets

(51) Int. Cl.
*C07C 29/151* (2006.01)
*G01N 31/10* (2006.01)

(52) U.S. Cl.
CPC .............. *G06Q 50/04* (2013.01); *Y02E 50/32* (2013.01); *Y02P 90/30* (2015.11); *Y10T 436/204165* (2015.01)

(56) References Cited

FOREIGN PATENT DOCUMENTS

| JP | 2008-260832 | 10/2008 |
|----|-------------|---------|
| JP | 2009-215505 | 9/2009 |
| JP | 2010-502191 | 1/2010 |
| JP | 2011-514236 | 5/2011 |
| JP | 2011-514927 | 5/2011 |
| JP | 2012-516152 | 7/2012 |
| WO | 01/72611 | 10/2001 |
| WO | 2008/028055 | 3/2008 |
| WO | 2009/095693 | 8/2009 |
| WO | 2009/111026 | 9/2009 |
| WO | 2010/093262 | 8/2010 |

OTHER PUBLICATIONS

Demirbaş, Ayhan. "Calculation of higher heating values of biomass fuels." Fuel 76.5 (1997): 431-434.*

Bratbak, G. U. N. N. A. R., and I. A. N. Dundas. "Bacterial dry matter content and biomass estimations." Appl. Environ. Microbiol. 48.4 (1984): 755-757.*

International Search Report dated Oct. 15, 2013 in International (PCT) Application No. PCT/JP2013/075292.

He, Jie, and Wennan Zhang. "Techno-economic evaluation of thereto-chemical biomass-to-ethanol", Applied Energy, vol. 88, No. 4, 2011, pp. 1224-1232.

Office Action dated Sep. 26, 2017 in Japanese Application No. 2014-536902, with English translation.

\* cited by examiner

PRODUCTIVITY EVALUATION METHOD, PRODUCTIVITY EVALUATION DEVICE, PROGRAM, AND RECORDING MEDIUM

TECHNICAL FIELD

The present invention relates to a productivity evaluation method, a productivity evaluation device, a program, and a recording medium. Particularly, the present invention relates to a method and a device for evaluating the productivity of a chemical substance, as well as a program for causing a computer to function as the productivity evaluation device, and a recording medium recording the program.

This application claims priority from Japanese Patent Application No. 2012-206979 filed on Sep. 20, 2012, the content of which is incorporated herein by reference.

BACKGROUND ART

In the field of production of chemical substances such as ethanol, the technique to convert a waste material into a chemical substance by a catalytic reaction after gasification of the waste material has been being developed, and various relevant techniques are known (see, for example, Patent Document 1).

For example, Patent Document 1 describes a waste regeneration treatment method in which a waste material, such as food residue, woody biomass, rice hull, agricultural residue, activated sludge, and waste plastic, is carbonated and also regenerated into useful liquid fuel. More specifically, in this method, a solid waste material is charged together with superheated steam into a carbonization-gasification furnace which is tilted downwardly as viewed from an inlet toward an outlet.

In this method, a waste material is carbonized by thermal decomposition without burning by indirectly heating the waste material being shut-off from air in the carbonization-gasification furnace by using an electric heater. In the furnace, the accumulated amount of the carbonized waste material is caused to increase toward the outlet, and a water gas shift reaction is caused by heat of the carbide to produce and dry distillation gas composed mainly of hydrogen and carbon monoxide. Then, in this method, the dry distillation gas was converted into liquid fuel by using Fischer-Tropsch synthesis catalyst.

PRIOR ART DOCUMENTS

Patent Documents

Patent Document 1: Japanese Unexamined Patent Application, Publication No. 2008-260832

DISCLOSURE OF INVENTION

Problems to be Solved by the Invention

In the business where chemical substances such as ethanol are produced from waste materials, it has been desired to visualize the productivity of the chemical substance. However, in such field, no method is known which enables efficient evaluation of the productivity of a chemical substance in the production of a chemical substance such as ethanol from a waste material.

Means for Solving the Problems (1) The productivity evaluation method of the present invention according to the first embodiment is a method for evaluating productivity of a chemical substance in a process including a first step of obtaining gas from a waste material and a second step of synthesizing a chemical substance from, as a raw material, the gas obtained in the first step in the presence of a catalyst, said method including:

a first carbon mass calculation stage of calculating mass of carbon contained in the waste material, a second carbon mass calculation stage of calculating mass of carbon contained in the chemical substance produced in said process, and a productivity evaluation stage of evaluating the productivity of the chemical substance based on values of the mass of carbon which are calculated in the first carbon mass calculation stage and the second carbon mass calculation stage.

(2) The productivity evaluation method of the present invention according to the first embodiment is the method according to (1), further including:

a third carbon mass calculation stage of calculating mass of carbon contained in the gas obtained in the first step of said process, and a fourth carbon mass calculation stage of calculating mass of carbon contained in a residue of the waste material resulting from the first step of said process, wherein, in the first carbon mass calculation stage, the mass of carbon contained in the waste material is calculated based on values of the mass of carbon which are calculated in the third carbon mass calculation stage and the fourth carbon mass calculation stage.

(3) The productivity evaluation method of the present invention according to the first embodiment is the method according to (2), wherein when a combustion improver is used in the first step of said process, said productivity evaluation method further including:

a fifth carbon mass calculation stage of calculating mass of carbon contained in the combustion improver used in the first step of said process, wherein in the first carbon mass calculation stage, mass of carbon contained in the waste material is calculated based on a value of the carbon mass which are calculated in the fifth carbon mass calculation stage.

That is, the productivity evaluation method of the present invention according to the first embodiment is the method according to (2), wherein when a combustion improver is used in the first step of said process, said productivity evaluation method further including:

a fifth carbon mass calculation stage of calculating mass of carbon contained in the combustion improver used in the first step of said process, wherein in the first carbon mass calculation stage, mass of carbon contained in the waste material is calculated based on values of the carbon mass which are calculated in the third carbon mass calculation stage, the fourth carbon mass calculation stage, and the fifth carbon mass calculation stage.

(4) The productivity evaluation method of the present invention according to the first embodiment is the method according to any one of (1) to (3), further including:

a carbon dioxide emission calculation stage of calculating an amount of carbon dioxide emission caused due to use of energy in the first step of said process, wherein in the productivity evaluation stage, the productivity of the chemical substance is evaluated based on a value of the amount of carbon dioxide emission calculated in the carbon dioxide emission calculation stage.

That is, the productivity evaluation method of the present invention according to the first embodiment is the method according to any one of (1) to (3), further including:

a carbon dioxide emission calculation stage of calculating an amount of carbon dioxide emission caused due to use of energy in the first step of said process, wherein in the productivity evaluation stage, the productivity of the chemical substance is evaluated based on values of the carbon mass which are calculated in the first carbon mass calculation stage and the second carbon mass calculation stage and a value of the amount of carbon dioxide emission calculated in the carbon dioxide emission calculation stage.

(5) The productivity evaluation method of the present invention according to the first embodiment is the method according to any one of (1) to (4), wherein the chemical substance is a compound represented by the formula CxHyOz, so that mass of carbon contained in the compound CxHyOz is calculated in the second carbon mass calculation stage and that the productivity of the compound CxHyOz is evaluated in the productivity evaluation stage.

(6) The charging system of the present invention according to the second embodiment is a system which determines a charge for a waste material depending on the productivity of the chemical substance evaluated by the productivity evaluation method according to any one of (1) to (5).

(7) The productivity evaluation device of the present invention according to the third embodiment is a device for evaluating productivity of a chemical substance in a process including a first step of obtaining gas from a waste material and a second step of synthesizing a chemical substance from, as a raw material, the gas obtained in the first step in the presence of a catalyst, said device including:

a first carbon mass calculation unit for calculating mass of carbon contained in the waste material, a second carbon mass calculation unit for calculating mass of carbon contained in the chemical substance produced in said process, and a productivity evaluation unit for evaluating the productivity of the chemical substance based on values of the carbon mass which are calculated in the first carbon mass calculation stage and the second carbon mass calculation stage.

(8) The program of the present invention according to the fourth embodiment is a program for evaluating productivity of a chemical substance in a process including a first step of obtaining gas from a waste material and a second step of synthesizing a chemical substance from, as a raw material, the gas obtained in the first step in the presence of a catalyst, said program causing a computer to perform functions of:

a first carbon mass calculation unit for calculating mass of carbon contained in the waste material, a second carbon mass calculation unit for calculating mass of carbon contained in the chemical substance produced in said process, and a productivity evaluation unit for evaluating the productivity of the chemical substance based on values of the carbon mass which are calculated in the first carbon mass calculation stage and the second carbon mass calculation stage.

(9) The fifth embodiment of the present invention is a recording medium having recorded therein a computer program for evaluating productivity of a chemical substance in a process including a first step of obtaining gas from a waste material and a second step of synthesizing a chemical substance from, as a raw material, the gas obtained in the first step in the presence of a catalyst, said program causing a computer to perform functions of:

a first carbon mass calculation unit for calculating mass of carbon contained in the waste material, a second carbon mass calculation unit for calculating mass of carbon contained in the chemical substance produced in said process, and a productivity evaluation unit for evaluating the productivity of the chemical substance based on values of the carbon mass which are calculated in the first carbon mass calculation stage and the second carbon mass calculation stage.

The gist of the invention described above does not necessarily enumerate all necessary features of the present invention.

The subcombinations of any features described above may also belong to the present invention.

Effects of the Invention

As described above, according to the present invention, it is possible to efficiently evaluate the productivity of chemical substances such as ethanol in the production of such chemical substances from waste materials.

MODE FOR CARRYING OUT THE INVENTION

Hereinbelow, the present invention is described based on the embodiments of the invention. However, the embodiments below do not limit the invention according to the scope of claims, and that all combination of the features described in the embodiments are not necessarily essential to the means to solve the problems by the present invention.

The process of producing ethanol includes a first step of obtaining gas from a waste material and a second step of synthesizing a chemical substance from the gas in the presence of a catalyst. The waste material here can be classified roughly into a waste material derived from petroleum, such as a plastic; and a waste material derived from biological resources, such as domestic waste such as domestic flammable trash, paper waste, wood waste, sewage sludge, waste textile, pruned branch, animal and plant residues, animal and vegetable oils, meat and bone meal, waste solid fuel, excreta, wood chip, and organic sludge. Ethanol may be an example of the chemical substances and the compounds $C_xH_yO_z$ in this invention.

The first step of the process of producing ethanol is a step of converting a waste material into gas containing carbon monoxide and hydrogen by thermal decomposition and chemical reaction in a high temperature field. The high temperature field is, for example, a pyrolysis furnace or a melting furnace. In the first step, it is possible that a waste material is not converted completely and that residue is discharged. In the first step, a combustion improver may be used. The combustion improver is, for example, a liquefied petroleum gas, a light gas oil, coke, a mineral oil, a heavy oil, coal, a natural gas, kerosene, and a waste edible oil.

The second step of the process of producing ethanol is a step of introducing the synthesized gas, in which the composition ratio of carbon monoxide and hydrogen is adjusted, into a reactor filled with various catalysts, and synthesizing ethanol by heating the gas in the presence of a metal catalyst or by heating or cooling the gas in the presence of a microbial catalyst. The ethanol is produced in a gaseous state if a metal catalyst is used, because the synthesis reaction is carried out at a high temperature. On the other hand, if a microbial catalyst is used, the ethanol is produced in a liquid state, because the synthesis reaction is carried out at a temperature that does not to kill the microbe. In the second step, various by-products, such as acetaldehyde, acetic acid, methanol and methane, are formed as well as ethanol.

Figure 1:
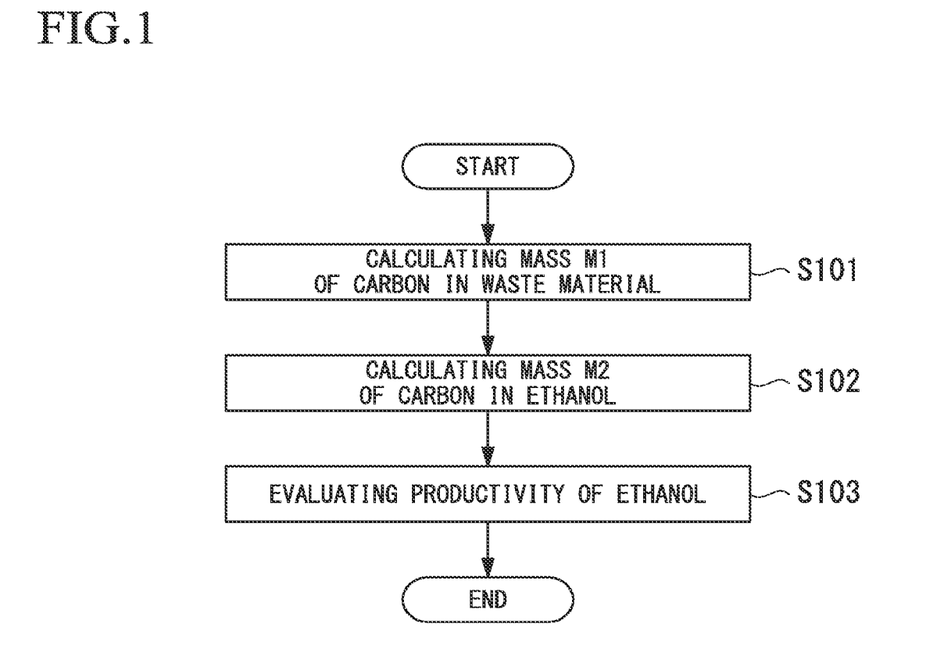
FIG. 1 is a drawing showing an example of procedure of a productivity evaluation method according to the first embodiment.

FIG. 1 shows an example of procedure of the productivity evaluation method according to the first embodiment. Referring to this drawing, detailed descriptions are given below with respect to the method of evaluating the productivity of ethanol in production thereof by the aforementioned process.

First, in this evaluation method, the mass M1 of carbon contained in the waste material is calculated (step "S101"). For example, the mass M1 of carbon in the waste material can be calculated by multiplying the total weight of the waste material by the ratio of the mass of carbon in the waste material to the total weight of the waste material.

The total weight of the waste material can be calculated by, for example, subtracting the weight of a garbage truck not loaded with the waste material from the weight of the same garbage truck loaded with the waste material. Alternatively, the mass of the waste material can be, for example, calculated by multiplying the volume of the waste material by the densities of the components of the waste material, provided that the types of the components of the waste material are known.

On the other hand, the ratio of carbon in the waste material to the total waste material can be, for example, calculated by an elemental analysis method. The elemental analysis method is a method of determining the composition ratios of the specific elements. For example, when an organic compound composed of C (carbon), H (hydrogen), and O (oxygen) is combusted completely, all of the C atoms in the compound form $CO_2$ and all of the H atoms in the compound form $H_2O$. Therefore, the composition formula of an organic compound composed of C, H, and O can be obtained from the masses of the water and the carbon dioxide that result from the combustion of the organic compound. Regarding the mass of carbon, it can be calculated by collecting the carbon dioxide, measuring the total mass of the carbon dioxide, and multiplying the total mass by the ratio of the atomic weight of carbon/the molecular weight of $CO_2$. In the case that the ratios of the weight of a waste material derived from biological resources and the weight of a waste material derived from petroleum, relative to the total weight of the waste material, are known, the ratio of the mass of carbon in the waste material to the total weight of the waste material can be calculated by, for example, adding the product of (mass ratio of the waste material component derived from biological resources in the whole waste material×mass ratio of the carbon in the waste material component derived from biological resources) to the product of (mass ratio of the waste material component derived from petroleum in the whole waste material×mass ratio of the carbon in the waste material component derived from petroleum). In the case that a place(s) where the waste material is collected is known, the ratio of the mass of carbon in the waste material to the total weight of the waste material can be, for example, determined by referring to a database showing the ratio of the mass of carbon in the waste material to the total weight of the waste material for each collecting place, which have been calculated in advance in such manner as described above.

Next, in this method, the mass M2 of carbon in the ethanol produced by the process described above is calculated (step "S102"). For example, the mass M2 of carbon in ethanol can be calculated by multiplying the weight of ethanol by the ratio of the mass of carbon atoms to the mass of ethanol molecule.

Then, in this method, the productivity of ethanol is evaluated based on the mass M1 of carbon calculated in the step S101 and the mass M2 of carbon calculated in the step S102 (step "S103"). For example, the productivity of ethanol is evaluated based on a value obtained by dividing the mass M1 of carbon by the mass M2 of carbon, that is, the ratio of the mass M2 of carbon in the ethanol produced from the waste material to the mass M1 of carbon in the waste material. For example, in the case that the ratio of the mass M2 of carbon in the ethanol produced from the waste material to the mass M1 of carbon in the waste material is X (%), the productivity of the ethanol, i.e., the level of efficiency of ethanol production from the waste material, is evaluated as X (%).

Figure 2:
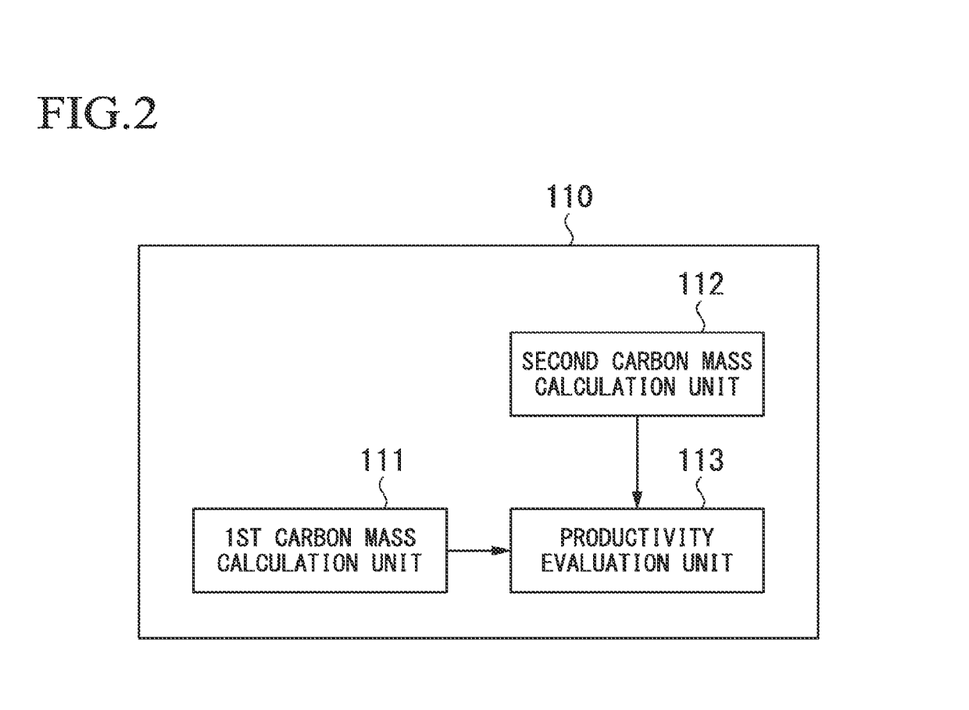
FIG. 2 is a drawing showing an example of block configuration of a productivity evaluation device 110 according to the first embodiment.

FIG. 2 shows an example of block configuration of a productivity evaluation device 110 according to the first embodiment. The productivity evaluation device 110 is a device for evaluating the productivity of ethanol. The productivity evaluation device 110 according to the first embodiment includes a first carbon mass calculation unit 111, a second carbon mass calculation unit 112, and a productivity evaluation unit 113. The detailed descriptions are given below with respect to the functions and motions of each of the components.

The first carbon mass calculation unit 111 calculates the mass M1 of carbon in the waste material.

The second carbon mass calculation unit 112 calculates the mass M2 of carbon in ethanol.

The productivity evaluation unit 113 evaluates the productivity of ethanol based on the mass M1 of carbon calculated by the first carbon mass calculation unit 111 and the mass M2 of carbon calculated by the second carbon mass calculation unit 112.

Referring to FIG. 1 and FIG. 2, detailed descriptions are given below with respect to a process of evaluating the productivity of ethanol by the productivity evaluation device 110 according to the first embodiment.

The first carbon mass calculation unit 111 of the productivity evaluation device 110 calculates the mass M1 of carbon in the waste material (step "S101"). For example, the first carbon mass calculation unit 111 calculates the mass M1 of carbon in the waste material by multiplying the weight of the waste material by the ratio of the mass of carbon in the waste material to the total weight of the waste material.

For example, the first carbon mass calculation unit 111 may receive input of the information on the weight of a garbage truck loaded with the waste material and the information on the weight of the same garbage truck not loaded with the waste material. The information may be, for example, input via an input device such as a keyboard, a mouse, or a touch panel, or input from a measuring device for measuring the weight of a garbage truck. The first carbon mass calculation unit 111 calculates the weight of the waste material by subtracting the weight of a garbage truck not loaded with the waste material from the weight of the same garbage truck loaded with the waste material.

Alternatively, for example, the first carbon mass calculation unit 111 may receive input of the information on the volume of the waste material and the information on the densities of the components of the waste material. The information on the volume of the waste material may be, for example, input via an input device such as a keyboard, a mouse, or a touch panel, or input from a measuring device for measuring the volume of the waste material. The information on the densities of the components of the waste material may be, for example, input via an input device such as a keyboard, a mouse, or a touch panel, or input from a measuring device for measuring the densities of the components of the waste material. The first carbon mass calculation unit 111 calculates the weight of the waste material by multiplying the volume of the waste material by the densities of the components of the waste material.

Further, for example, the first carbon mass calculation unit 111 may receive input of the information on the ratio of carbon in the waste material to the total waste material, which is calculated by an elemental analysis method. The information may be, for example, input via an input device such as a keyboard, a mouse, or a touch panel, or input from an elemental analysis device.

Furthermore, for example, the first carbon mass calculation unit 111 may receive input of the information on the ratio of the weight of the waste material derived from biological resources in the waste material to the total weight of the waste material, the information on the ratio of the weight of the waste material derived from petroleum in the waste material to the total weight of the waste material, the information on the ratio of the mass of the carbon in the waste material derived from biological resources to the total weight of the waste material derived from biological resources, and the information on the ratio of the mass of the carbon in the waste material from petroleum to the total weight of the waste material derived from petroleum. The information may be, for example, input via an input device such as a keyboard, a mouse, or a touch panel. The first carbon mass calculation unit 111 calculates the ratio of the mass of carbon in the waste material to the total weight of the waste material by, for example, adding the product of (mass ratio of a waste material derived from biological resources in the waste material to the total weight of the waste material×mass ratio of the carbon in the waste material derived from biological resources to the total weight of the waste material derived from biological resources) to the product of (mass ratio of a waste material derived from petroleum in the waste material to the total weight of the waste material×mass ratio of the carbon in the waste material derived from petroleum to the total weight of the waste material derived from petroleum).

Furthermore, for example, the first carbon mass calculation unit 111 may receive input of the information on the place(s) where the waste material is collected. This information may be, for example, input via an input device such as a keyboard, a mouse, or a touch panel. The first carbon mass calculation unit 111 determines the ratio of the mass of carbon in the waste material to the total weight of the waste material by referring to a database showing the ratio of the mass of carbon in the waste material to the total weight of the waste material for each collecting place, which have been calculated in advance in such matter as described above.

The first carbon mass calculation unit 111 calculates the mass M1 of carbon in the waste material by multiplying the weight of the waste material by the mass ratio of carbon in the waste material. The first carbon mass calculation unit 111 transmits the data of the calculated mass M1 of carbon to the productivity evaluation unit 113.

The second carbon mass calculation unit 112 of the productivity evaluation device 110 calculates the mass M2 of carbon in the ethanol produced by the process described above (step "S102"). For example, the second carbon mass calculation unit 112 receives input of the information on the weight of ethanol. This information may be, for example, input via an input device such as a keyboard, a mouse, or a touch panel, or input from a measuring device for measuring the weight of ethanol. The second carbon mass calculation unit 112 calculates the mass M2 of carbon in ethanol by multiplying the weight of ethanol by the ratio of the mass of carbon atoms in ethanol to the mass of ethanol molecule. The second carbon mass calculation unit 112 transmits the data of the calculated mass M2 of carbon to the productivity evaluation unit 113.

The productivity evaluation unit 113 of the productivity evaluation device 110 receives each of the data from the first carbon mass calculation unit 111 and the data from the second carbon mass calculation unit 112. The productivity evaluation unit 113 evaluates the productivity of ethanol based on the mass M1 of carbon shown in the data from the first carbon mass calculation unit 111 and the mass M2 of carbon shown in the data from the second carbon mass calculation unit 112 (step "S103"). For example, the productivity evaluation unit 113 evaluates the productivity of ethanol based on the value obtained by dividing the mass M1 of carbon by the mass M2 of carbon, that is, the ratio of the mass M2 of carbon in the ethanol produced from the waste material to the mass M1 of carbon in the waste material. For example, in the case that the ratio of the mass M2 of carbon in the ethanol produced from the waste material to the mass M1 of carbon in the waste material is X (%), the productivity evaluation unit 113 evaluates the level of the productivity of ethanol, i.e., the efficiency of ethanol production from the waste material, to be X (%).

As described above, for evaluating productivity of ethanol in a process including a first step of obtaining gas from a waste material and a second step of chemically synthesizing ethanol from the gas obtained in the first step in the presence of a catalyst, the productivity evaluation method according to the first embodiment includes a step of calculating the mass of carbon in the waste material. This method further includes a step of evaluating the productivity of ethanol based on the mass of carbon in the waste material and the mass of carbon in the ethanol.

Thus, according to the productivity evaluation method of the first embodiment, the productivity of ethanol in the production thereof from a waste material can be efficiently evaluated.

Figure 3:
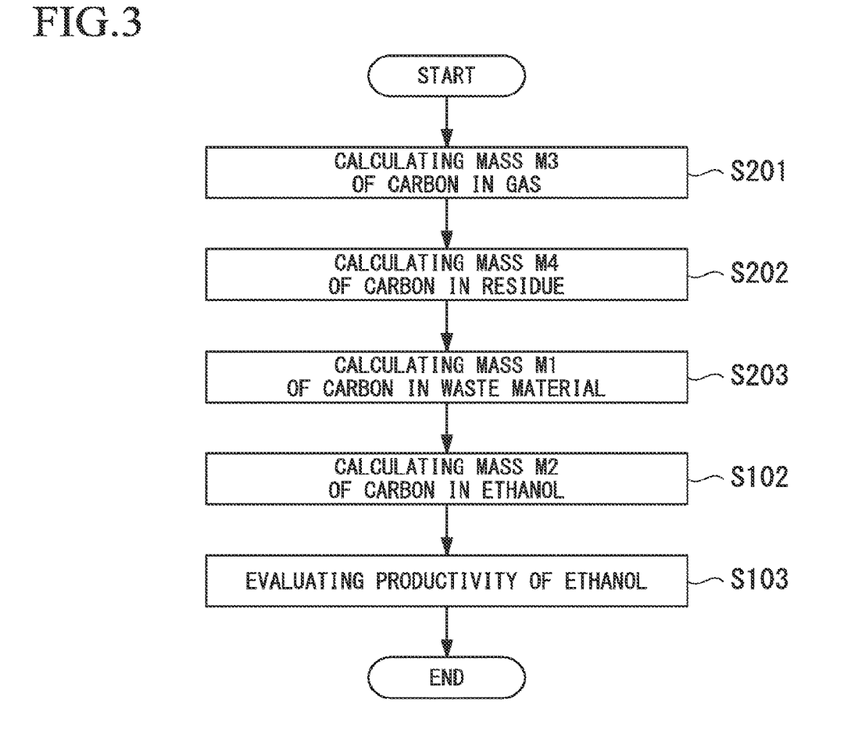
FIG. 3 is a drawing showing an example of procedure of a productivity evaluation method according to the second embodiment.

FIG. 3 shows an example of procedure of the productivity evaluation method according to the second embodiment. Referring to this drawing, detailed descriptions are given below with respect to the method of evaluating the productivity of ethanol where the mass M1 of carbon in the waste material is calculated in a different manner from the first embodiment. In the descriptions given below, reference is made to FIG. 1 as well. Through FIG. 3 and FIG. 1, the same "S"-prefixed reference numerals designate the same steps.

First, in this method, the mass M3 of carbon in the gas obtained in the first step of the production process described above is calculated (step "S201"). For example, the mass M3 of carbon in the gas can be calculated by multiplying the mass of a carbon-containing molecule in the gas by the ratio of the mass of carbon atoms to the mass of the molecule. In the case that more than one kind of molecule are contained in the gas, the mass M3 of carbon in the gas can be calculated by multiplying the mass of the molecule by the mass ratio of the carbon atoms to the molecule with respect to each of the different types of molecule, and adding up all of the obtained values.

With respect to each of the different types of molecules in the gas, the mass of the molecule can be, for example, calculated by multiplying the mass of gas and the ratio of the mass of the molecule in the gas to the total mass of the gas. The ratio of the mass of each of the molecules in the gas to the total mass of the gas can be, for example, obtained by analysis using a gas chromatography detection apparatus. On the other hand, the mass of the gas can be, for example, calculated by using a gas state equation if the pressure, temperature, and volume of the gas flowing in the pipe are known. The volume of the gas can be, for example, calculated by multiplying the cross-sectional area of the pipe by the flow rate of the gas and the period of time during which the gas continues to flow.

Next, in this method, the mass M4 of carbon contained in the residue discharged in the first step of the production process described above (step "S202"). For example, the mass M4 of carbon in the residue can be calculated based on the mass of the residue, kinds of atoms in the residue and the mass ratio of carbon in the residue. The kinds of atoms in the residue and the mass ratio of carbon in the residue can be, for example, analyzed by an elemental analysis method.

Then, in this method, the mass M1 of carbon in the waste material is calculated based on the mass M3 of carbon calculated in the step S201 and the mass M4 of carbon calculated in the step S202 (step "S203"). For example, the mass M1 of carbon in the waste material can be calculated by adding the mass M3 of carbon in the gas to the mass M4 of carbon in the residue. For example, the calculation of the mass M1 of carbon in the waste material can be performed not simply by adding the mass M3 of carbon in the gas to the mass M4 of carbon in the residue, but also by referring to the efficiency of obtaining the gas from the waste material or the like which is experimentally calculated in advance.

In this method, as in the productivity evaluation method according to the first embodiment, the mass M2 of carbon in ethanol is calculated (step "S102"), and the productivity of ethanol is evaluated based on the mass M1 of carbon in the waste material and the mass M2 of carbon in ethanol (step "S103").

Figure 4:
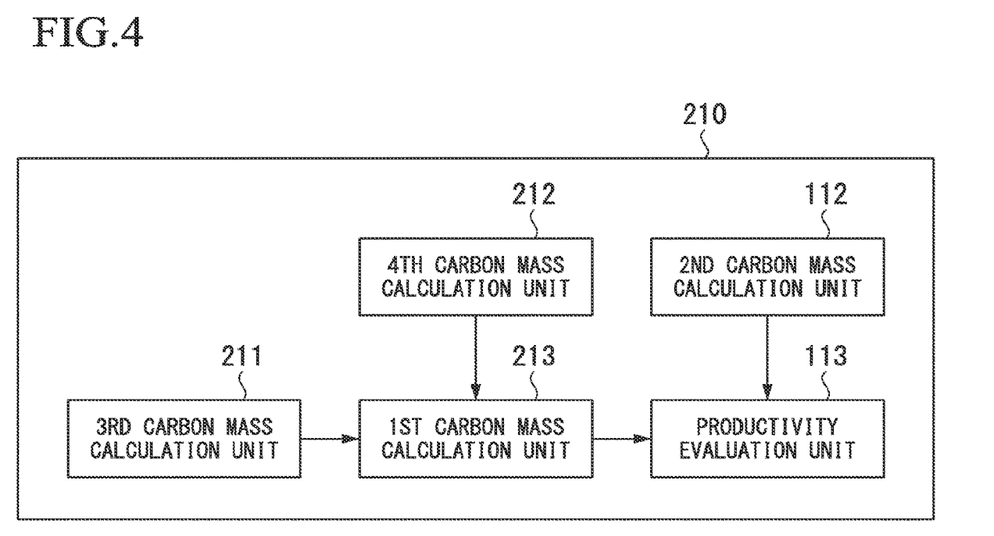
FIG. 4 is a drawing showing an example of block configuration of a productivity evaluation device 210 according to the second embodiment.

FIG. 4 shows an example of block configuration of a productivity evaluation device 210 according to the second embodiment. The productivity evaluation device 210 according to the second embodiment includes a third carbon mass calculation unit 211, a fourth carbon mass calculation unit 212, a first carbon mass calculation unit 213, a second carbon mass calculation unit 112, and a productivity evaluation unit 113. Detailed descriptions are given below with respect to the functions and actions of the respective components.

With respect to the productivity evaluation device 210 shown in FIG. 4 and the productivity evaluation device 110 in FIG. 2, the identically termed components designated with the same reference numerals have the same functions and actions.

The third carbon mass calculation unit 211 calculates the mass M3 of carbon in the gas obtained in the first step of the production process described above.

The fourth carbon mass calculation unit 212 calculates the mass M4 of carbon in the residue discharged in the first step of the production process described above.

The first carbon mass calculation unit 213 calculates the mass M1 of carbon in the waste material based on the mass M3 of carbon calculated by the third carbon mass calculation unit 211 and the mass M4 of carbon calculated by the fourth carbon mass calculation unit 212.

Referring to FIG. 3 and FIG. 4, detailed descriptions are given below with respect to the process of evaluating the productivity of ethanol by the productivity evaluation device 210 according to the second embodiment.

The third carbon mass calculation unit 211 of the productivity evaluation device 210 calculates the mass M3 of carbon in the gas obtained in the first step of the production process (step "S201"). For example, the third carbon mass calculation unit 211 calculates the mass M3 of carbon in the gas by multiplying the mass of a carbon-containing molecule in the gas by the ratio of the mass of carbon atoms to the mass of the molecule. In the case that more than one kind of molecules are contained in the gas, the third carbon mass calculation unit 211 calculates the mass M3 of carbon in the gas as following. Regarding each of the different kinds of molecules, the third carbon mass calculation unit 211 multiplies the mass of the molecule by the ratio of the mass of carbon atoms to the mass of the molecule. All of the thus obtained values are added up to determine the mass M3 of carbon in the gas.

For example, the third carbon mass calculation unit 211 calculates the mass of each of the molecules in the gas by multiplying the mass of gas and the ratio of mass of the molecule in the gas to the total mass of the gas.

For example, the third carbon mass calculation unit 211 may receive input of the information on the respective ratios of the molecules in the gas to the total of the gas. This information may be, for example, input via an input device such as a keyboard, a mouse, or a touch panel, or input from a gas chromatography detection apparatus.

Alternatively, for example, the third carbon mass calculation unit 211 may receive input of the information on the pressure, temperature, and volume of the gas flowing in the pipe. The information on the pressure may be, for example, input via an input device such as a keyboard, a mouse, or a touch panel, or input from a measuring device for measuring pressure in the pipe. The information on the temperature may be, for example, input via an input device such as a keyboard, a mouse, or a touch panel, or input from a measuring device for measuring temperature in the pipe. The information on the volume may be, for example, input via an input device such as a keyboard, a mouse, or a touch panel, or input from a measuring device for measuring volume flow rate in the pipe, or calculated by multiplying the cross-sectional area of the pipe by the flow rate of the gas and the period of time during which the gas continues to flow. The third carbon mass calculation unit 211 calculates the mass of gas by a gas state equation based on the aforementioned information.

The third carbon mass calculation unit 211 calculates the mass M3 of carbon in the gas by multiplying the mass of a carbon-containing molecule in the gas by the ratio of the mass of carbon atom(s) to the mass of the molecule, and then, transmits the data of the calculated mass M3 of carbon to the first carbon mass calculation unit 213.

The fourth carbon mass calculation unit 212 of the productivity evaluation device 210 calculates the mass M4 of carbon in the residue discharged in the first step of the production process described above (step "S201"). For example, the fourth carbon mass calculation unit 212 calculates the mass M4 of carbon in the residue discharged based on the mass of the residue, kinds of atoms in the residue and the ratio of the mass of carbon in the residue.

Further, for example, the fourth carbon mass calculation unit 212 may receive input of the information on the mass of the residue, kinds of atoms in the residue and the ratio of the mass of carbon in the residue. The information on the mass of residue may be, for example, input via an input device such as a keyboard, a mouse, or a touch panel, or input from a measuring device for measuring the weight of the residue. The information on the kinds of atoms in the residue and the information on the ratio of the mass of carbon in the residue may be, for example, input via an input device such as a keyboard, a mouse, or a touch panel, or input from an elemental analyzer.

The fourth carbon mass calculation unit 212 calculates the mass M4 of carbon in the residue based on the mass of the residue, kinds of atoms in the residue and the ratio of the mass of carbon in the residue, and then, transmits the data of the calculated mass M4 of carbon to the first carbon mass calculation unit 213.

The first carbon mass calculation unit 213 of the productivity evaluation device 210 receives each of the data transmitted from the third carbon mass calculation unit 211 and the data transmitted from the fourth carbon mass calculation unit 212, and then, calculates the mass M1 of carbon in the waste material based on the mass M3 of carbon shown in the data transmitted from the third carbon mass calculation unit 211 and the mass M4 of carbon shown in the data transmitted from the fourth carbon mass calculation unit 212 (step "203"). For example, the first carbon mass calculation unit 213 calculates the mass M1 of carbon in the waste material by adding the mass M3 of carbon in the gas to the mass M4 of carbon in the residue. Alternatively, for example, the first carbon mass calculation unit 213 may calculate the mass M1 of carbon in the waste material by referring to the efficiency of obtaining the gas from the waste material and the like which is experimentally calculated in advance.

In the productivity evaluation device 210 according to the second embodiment, as in the productivity evaluation device 110 according to the first embodiment, the mass M2 of carbon in ethanol is calculated (step "S102"), and then, the productivity of ethanol is evaluated based on the mass M1 of carbon in the waste material and the mass M2 of carbon in ethanol (step "S103").

As described above, in the productivity evaluation method according to the second embodiment, the mass M3 of carbon in the gas obtained in the first step of the production process described above is calculated. In this method, the mass M4 of carbon in the residue discharged in the first step of the production process described above is calculated. In this method, the mass M1 of carbon in the waste material is calculated based on the mass M3 of carbon in the gas and the mass M4 of carbon in the residue.

Thus, according to the productivity evaluation method according to the second embodiment, the mass M3 of carbon in the gas obtained in the first step of the production process described above and the mass M4 of carbon in the residue discharged in the first step of the production process described above can be easily calculated. Therefore, the mass M1 of carbon in the waste material can be calculated more easily and more precisely, as compared to the productivity evaluation method according to the first embodiment. Consequently, the productivity of ethanol can be evaluated more easily and more precisely.

Figure 5:
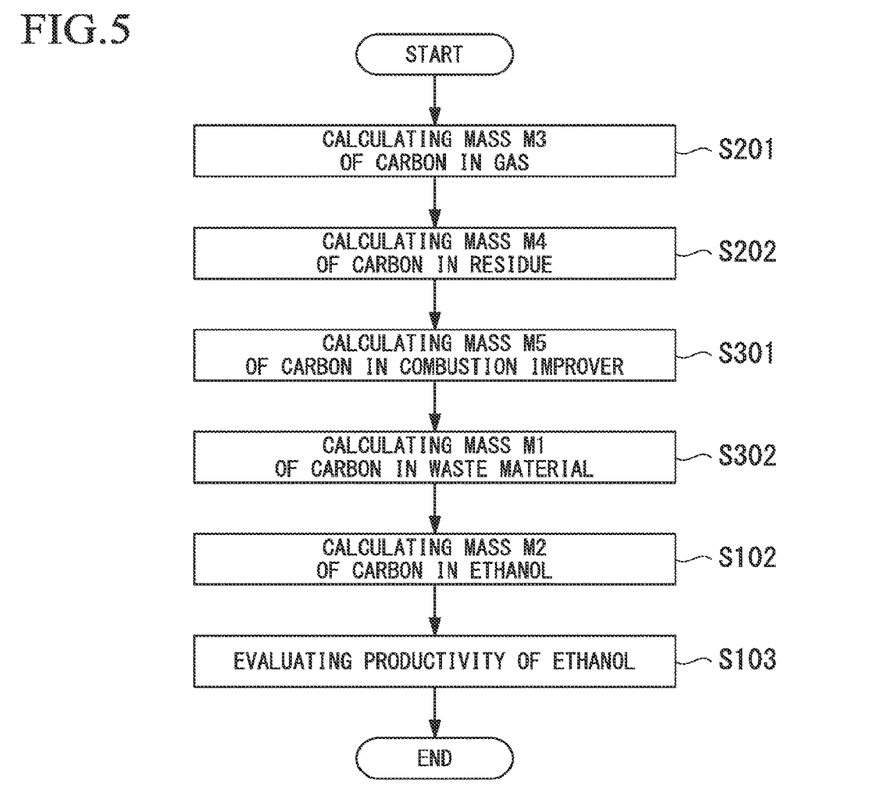
FIG. 5 is a drawing showing an example of procedure of a productivity evaluation method according to the third embodiment.

FIG. 5 is a drawing showing an example of procedure of the productivity evaluation method according to the third embodiment. Referring to this drawing, detailed descriptions are given below with respect to a method of evaluating the productivity of ethanol in the case of using a combustion improver. In the descriptions given below, reference is made to FIG. 1 and FIG. 3 as well. Through FIG. 1, FIG. 3 and FIG. 5, the same "S"-prefixed reference numerals designate the same steps.

First, in this method, as in the productivity evaluation method according to the second embodiment, the mass M3 of carbon in the gas obtained in the first step of the production process described above is calculated (step "S201"), and the mass M4 of carbon in the residue discharged in the first step of the production process described above (step "S202").

Next, in this method, the mass M5 of carbon in the combustion improver used in the first step of the production process described above is calculated (step "S301"). For example, the mass M5 of carbon in the combustion improver can be calculated by multiplying the mass of the combustion improver by the ratio of the mass of carbon atom to the total mass of the combustion improver.

Then, in this method, the mass M1 of carbon in the waste material is calculated based on the mass M3 of carbon calculated in the step S201, the mass M4 of carbon calculated in the step S202, and the mass M5 of carbon calculated in the step S301 (step "S302"). For example, the mass M1 of carbon in the waste material can be calculated by adding the mass M3 of carbon in the gas to the mass M4 of carbon in the residue and subtracting therefrom the mass M5 of carbon in the combustion improver.

In this method, as in the productivity evaluation method according to the first embodiment, the mass M2 of carbon in the ethanol is calculated (step "S102"), and then, the productivity of ethanol is evaluated based on the mass M1 of carbon in the waste material and the mass M2 of carbon in the ethanol (step "S103").

Figure 6:
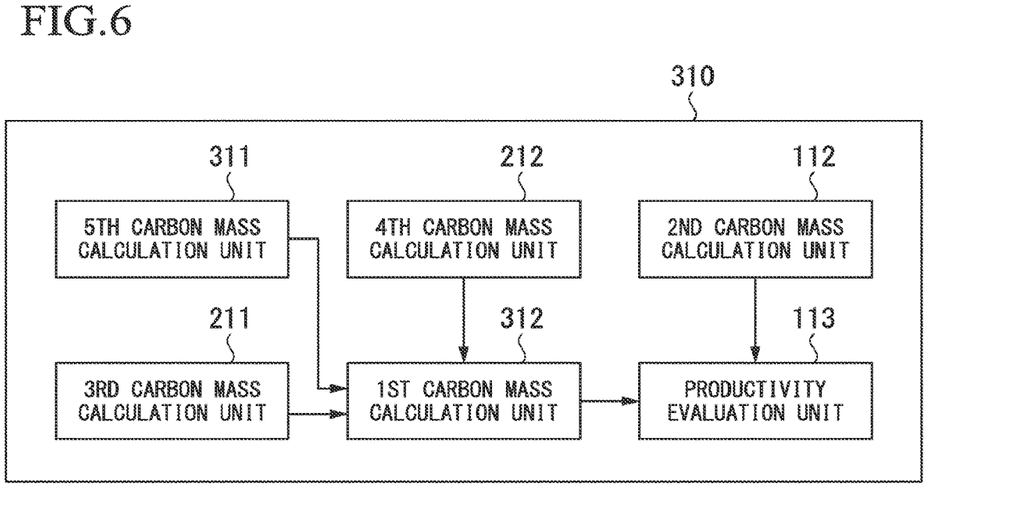
FIG. 6 is a drawing showing an example of block configuration of a productivity evaluation device 310 according to the third embodiment.

FIG. 6 shows an example of block configuration of a productivity evaluation device 310 according to the third embodiment. The productivity evaluation device 310 according to the third embodiment includes a third carbon mass calculation unit 211, a fourth carbon mass calculation unit 212, a fifth carbon mass calculation unit 311, a first carbon mass calculation unit 312, a second carbon mass calculation unit 112, and a productivity evaluation unit 113. Detailed descriptions are given below with respect to the functions and actions of each of the components.

With respect to the productivity evaluation device 310 shown in FIG. 6, the productivity evaluation device 110 in FIG. 2, and the productivity evaluation device 210 in FIG. 4, the identically termed components designated with the same reference numerals have the same functions and actions.

The fifth carbon mass calculation unit 311 calculates the mass M5 of carbon in the combustion improver used in the first step of the production process described above.

The first carbon mass calculation unit 312 calculates the mass M1 of carbon in the waste material based on the mass M3 of carbon calculated by the third carbon mass calculation unit 211, the mass M4 of carbon calculated by the fourth carbon mass calculation unit 212, and the mass M5 of carbon calculated by the fifth carbon mass calculation unit 311.

Referring to FIG. 5 and FIG. 6, the detailed descriptions are made with respect to the process of evaluating the productivity of ethanol by the production evaluation device 310 according to the third embodiment.

First, the productivity evaluation device 310 according to the third embodiment, as in the productivity evaluation device 210 according to the second embodiment, calculates the mass M3 of carbon in the gas obtained in the first step of the production process described above (step "S201"). The productivity evaluation device 310 calculates the mass M4 of carbon in the residue discharged in the first step of the production process described above (step "S202").

The fifth carbon mass calculation unit 311 of the productivity evaluation device 310 calculates the mass M5 of carbon in the combustion improver used in the first step of the production process described above (step "S301"). For example, the fifth carbon mass calculation unit 311 calculates the mass M5 of carbon in the combustion improver by multiplying the mass of the combustion improver by the ratio of the mass of carbon atoms in the combustion improver to the total mass of the combustion improver.

For example, the fifth carbon mass calculation unit 311 receives input of the information on the mass of the combustion improver and the ratio of the mass of carbon atoms in the combustion improver to the total mass of the combustion improver. The information may be, for example, input via an input device such as a keyboard, a mouse, or a touch panel, or a detection device, or may be preset in the fifth carbon mass calculation unit 311.

The fifth carbon mass calculation unit 311 calculates the mass M5 of carbon in the combustion improver by multiplying the mass of the combustion improver by the ratio of the mass of carbon atoms in the combustion improver to the total mass of the combustion improver, and then, transmits the data of the calculated mass M5 of carbon to the first carbon mass calculation unit 312.

The first carbon mass calculation unit 312 of the productivity evaluation device 310 receives input of the data from the third carbon mass calculation unit 211, the data from the fourth carbon mass calculation unit 212, and the data from the fifth carbon mass calculation unit 311. The first carbon mass calculation unit 312 calculates the mass M1 of carbon in the waste material based on the mass M3 of carbon shown in the data from the third carbon mass calculation unit 211, the mass M4 of carbon shown in the data from the fourth carbon mass calculation unit 212, and the mass M5 of carbon shown in the data from the fifth carbon mass calculation unit 311 (step "S302"). For example, the first carbon mass calculation unit 312 calculates the mass M1 of carbon in the waste material by adding the mass M3 of carbon in the gas to the mass M4 of carbon in the residue, and subtracting therefrom the mass M5 of carbon in the combustion improver.

The productivity evaluation device 310 according to the third embodiment, as in the case of the productivity evaluation device 110 according to the first embodiment, calculates the mass M2 of carbon in the ethanol (step "S102"), and then, evaluates the productivity of ethanol based on the mass M1 of carbon in the waste material and the mass M2 of carbon in the ethanol (step "S103").

As described above, in the productivity evaluation method according to the third embodiment, when a combustion improver is used in the first step of the production process described above, the mass M5 of carbon in the combustion improver is calculated. Then, in this method, the mass M1 of carbon in the waste material is calculated based on the mass M3 of carbon in the gas, the mass M4 of carbon in the residue, and the mass M5 of carbon in the combustion improver.

Thus, according to the productivity evaluation method according to the third embodiment, the productivity of ethanol in the production thereof from a waste material can be efficiently evaluated even in the case of using a combustion improver.

Figure 7:
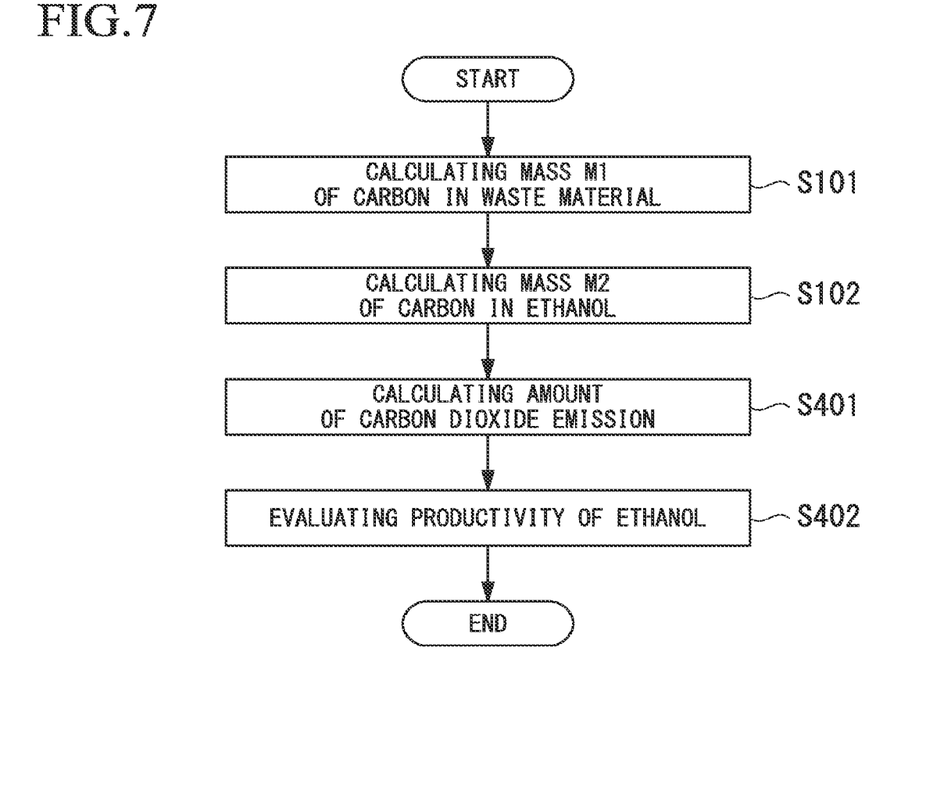
FIG. 7 is a drawing showing an example of procedure of a productivity evaluation method according to the fourth embodiment.

FIG. 7 is a drawing showing an example of procedure of a productivity evaluation method according to the fourth embodiment. Referring to this drawing, detailed descriptions are given below with respect to a method of evaluating the productivity of the ethanol in view of the amount of carbon dioxide emission caused due to the use of energy in the first step of the production process described above. In the descriptions given below, reference is made to FIG. 1 as well. Through FIG. 1 and FIG. 7, the same "S"-prefixed reference numerals designate the same steps.

First, in this method, as in the productivity evaluation method according to the first embodiment described above, the mass M1 of carbon in the waste material is calculated (step "S101"), and then, the mass M2 of carbon in the ethanol produced by the production process described above is calculated (step "S102").

Next, in this method, the amount of carbon dioxide emission caused due to the use of energy in the first step of the production process is calculated (step "S401"). For example, the amount of carbon dioxide emission caused due to the use of energy can be calculated by multiplying the amount of carbon dioxide emission per unit energy consumed in a pyrolysis furnace or a melting furnace by the actual amount of energy consumed in the pyrolysis furnace or the melting furnace.

Then, in this method, the productivity of ethanol is evaluated based on the mass M1 of carbon calculated in the step S101, the mass M2 of carbon calculated in the step S102, and the known amount of carbon dioxide emission calculated in the step S401 (step "S402"). For example, the productivity of ethanol is evaluated based on the value obtained by adding the mass M1 of carbon and the mass of carbon in the emitted carbon dioxide, and then, divided by the mass M2 of carbon. That is, the productivity of ethanol is evaluated based on the ratio of the mass M2 of carbon in the ethanol produced from the waste material to the total of the mass M1 of carbon in the waste material and the mass of carbon in the emitted carbon dioxide.

Figure 8:
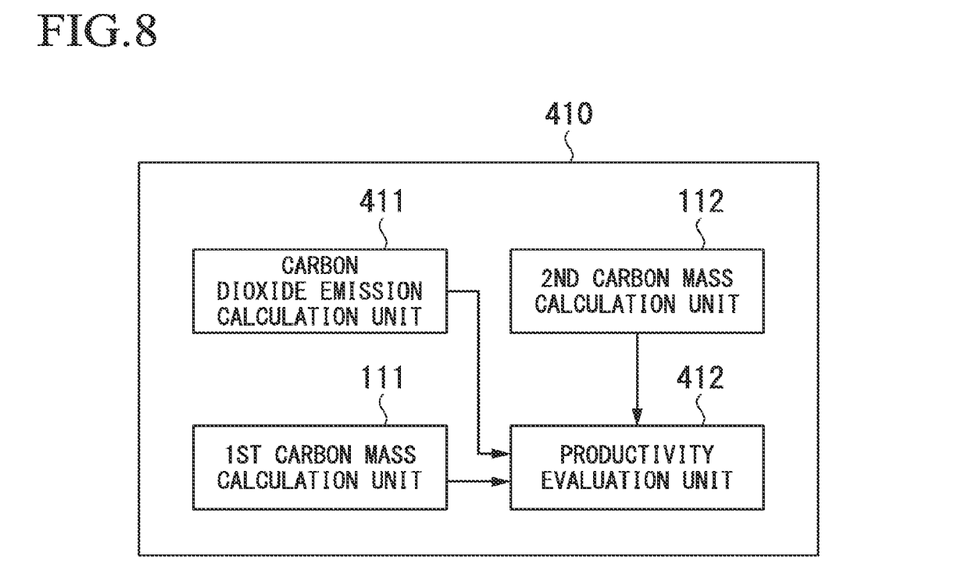
FIG. 8 is a drawing showing an example of block configuration of a productivity evaluation device 410 according to the fourth embodiment.

FIG. 8 shows an example of block configuration of a productivity evaluation device 410 according to the fourth embodiment. The productivity evaluation device 410 according to the fourth embodiment includes a first carbon mass calculation unit 111, a second carbon mass calculation unit 112, a carbon dioxide emission calculation unit 411, and a productivity evaluation unit 412.

Detailed descriptions are given below with respect to the functions and actions of each of the components.

With respect to the productivity evaluation device 410 shown in FIG. 8 and the productivity evaluation device 110 in FIG. 2, the identically termed components designated with the same reference numerals have the same functions and actions.

The carbon dioxide emission calculation unit 411 calculates the amount of carbon dioxide emission caused due to the use of energy in the first step of the production process described above.

The productivity evaluation unit 412 evaluates the productivity of ethanol based on the mass of carbon calculated by the first carbon mass calculation unit 111, the mass of carbon calculated by the second carbon mass calculation unit 112, and the amount of carbon dioxide emission calculated by the carbon dioxide emission calculation unit 411.

Referring to FIG. 7 and FIG. 8, detailed descriptions are given below with respect to how the productivity of ethanol is evaluated by the productivity evaluation device 410 according to the fourth embodiment.

First, in this method, as in the productivity evaluation device 110 according to the first embodiment described above, the productivity evaluation device 410 calculates the mass M1 of carbon in the waste material (step "S101"). The productivity evaluation device 410 calculates the mass M2 of carbon in the ethanol produced by the production process described above (step "S102").

The carbon dioxide emission calculation unit 411 of the productivity evaluation device 410 calculates the amount of carbon dioxide emission caused due to the use of energy in the first step of the production process described above (step "S401"). For example, the carbon dioxide emission calculation unit 411 calculates the amount of carbon dioxide emission caused due to the use of energy by multiplying the known amount of carbon dioxide emission per unit energy consumed in a pyrolysis furnace or a melting furnace by the actual amount of energy consumed in the pyrolysis furnace or the melting furnace.

For example, the carbon dioxide emission calculation unit 411 receives input of the information on the actual amount of energy consumed in the pyrolysis furnace or the melting furnace. This information may be, for example, input via an input device such as a keyboard, a mouse, or a touch panel, or input from a control device of the pyrolysis furnace or the melting furnace.

The carbon dioxide emission calculation unit 411 calculates the amount of carbon dioxide emission caused due to the use of energy by multiplying the known amount of carbon dioxide emission per unit energy consumed in a pyrolysis furnace or a melting furnace by the actual amount of energy consumed in the pyrolysis furnace or the melting furnace. The carbon dioxide emission calculation unit 411 transmits the data of the calculated amount of carbon dioxide emission to the productivity evaluation unit 412.

The productivity evaluation unit 412 receives each of the data transmitted from the first carbon mass calculation unit 111, the data transmitted from the second carbon mass calculation unit 112, and the data transmitted from the carbon dioxide emission calculation unit 411. The productivity evaluation unit 412 evaluates the productivity of ethanol based on the mass M1 of carbon shown in the data transmitted from the first carbon mass calculation unit 111, the mass M2 of carbon shown in the data transmitted from the second carbon mass calculation unit 112, the amount of carbon dioxide emission shown in the data transmitted from the carbon dioxide emission calculation unit 411 (step "S402"). For example, the productivity evaluation unit 412 evaluates the productivity of ethanol based on the value obtained by adding the mass M1 of carbon and the mass of carbon in the emitted carbon dioxide, and then, divided by the mass M2 of carbon. That is, the productivity evaluation unit 412 evaluates the productivity of ethanol based on the ratio of the mass M2 of carbon in the ethanol produced from the waste material to the total of the mass M1 of carbon in the waste material and the mass of carbon in the emitted carbon dioxide.

As described above, in the productivity evaluation method according to the fourth embodiment, the amount of carbon dioxide emission caused due to the use of energy in the first step of the production process described above is calculated. In this method, the productivity of ethanol is evaluated based on the mass of carbon in the waste material, the mass of carbon in ethanol, and the amount of carbon dioxide emission caused due to the use of energy in the first step of the production process described above.

Thus, according to the productivity evaluation method according to the fourth embodiment, the productivity of ethanol can be more efficiently evaluated, taking into consideration the amount of carbon dioxide emission which is caused due to the use of energy for recovering gas from the waste material.

The fifth embodiment relates to a charging (billing) system using the productivity evaluation method described above.

Generally, payment of service charge is required to have a waste material disposed. This charge is set according to the weight and type of the waste material. For example, the disposal of activated sludge generated from waste water treatment plants is generally implemented in either one of the following two ways. Specifically, the activated sludge having undergone dehydration and drying is brought to an incineration plant where the activated sludge is disposed, or the activated sludge after dehydration is disposed by conversion into a fertilizer or disposed in a landfill. However, the expensive disposal charge occurs in either case. The charge varies greatly depending on the systems of the treatment plant, the place of disposal, and the moisture content.

The actual waste material contains not only the components usable as raw materials (hydrogen and carbon monoxide), but also the components inhibiting the catalytic reaction in the second step in the production process of ethanol. Examples of the latter components (inhibitory components) include a S (sulfur) component such as hydrogen sulfide, and a Cl component such as hydrogen chloride. The ratio of the components inhibiting the catalytic reaction to the total of the waste material greatly depends on the waste material as the raw material. Generally, in the process of the second step, a mechanism trapping the inhibitory components is incorporated so that the presence of such inhibitory components in a small amount can be tolerated. However, if the ratio of the inhibitory components to the total of the waste material largely exceeds the capacity of the trapping mechanism, it is expected that the intrusion of inhibitory components in the second step influences the catalytic reaction. In this case, the productivity of ethanol is deteriorated.

That is, even if the ratio of the carbon to the total of the waste material is large, the productivity of ethanol is lowered when the amount of inhibitory components contained in the waste material is large. Therefore, it is desirable to construct a system of determining a charge depending on the amount of carbon in the waste material and the productivity of ethanol.

In view of this situation, a system according to the present embodiment determines the charge for disposal of the waste material based on the productivity obtained by any of the productivity evaluation methods according to the first to fourth embodiments. Specifically, as described above in connection with the productivity evaluation methods according to the first to fourth embodiments, the productivity of ethanol is calculated based on the mass of carbon in the waste material, the mass of carbon in the ethanol produced by said production process. If the calculated productivity of ethanol is higher than the predetermined value, a certain amount is discounted from the charge for disposal of the waste material.

The determination of whether a certain amount should be discounted from the charge for disposal of the waste material or not is made by the following method.

First, the present reaction for synthesizing ethanol is carried out using, as a raw material, a rice straw or wood containing almost no sulfur components nor chloride components which inhibit the catalytic reaction. The productivity of ethanol in this reaction is calculated based on the mass of carbon in the raw material and the mass of carbon in the converted ethanol. The calculated productivity of ethanol is recorded as the benchmark of the productivity of ethanol. Thereafter, according to any of the productivity evaluation methods according to the first to fourth embodiments, the productivity of ethanol is calculated based on the mass of carbon in the waste material, which is actually to be disposed, and the mass of carbon in the ethanol produced by said production process.

The charge for disposal is increased for the waste material when it is suggested that the waste material contains the inhibitory components and its productivity of ethanol is low according to the result of comparing the recorded benchmark of the productivity of ethanol with the productivity of ethanol of the waste material which is actually disposed. The charge for disposal is decreased for the waste material when the waste material has higher productivity than the recorded benchmark of the productivity of ethanol. The degree of increase or decrease of charge may be determined based on a linear conversion equation or the pre-set table showing the correlation of the productivity of ethanol and the degree of increase or decrease of charge. For example, the charge for disposal of the waste material may be calculated by the following Equation (1).

Charge for disposal of waste material=Basic Charge×(benchmark of productivity of ethanol−productivity of ethanol of waste material actually disposed)    (1)

According to the charging system according to the present embodiment, the charging system where the accurate productivity of ethanol is reflected can be constructed.

Figure 9:
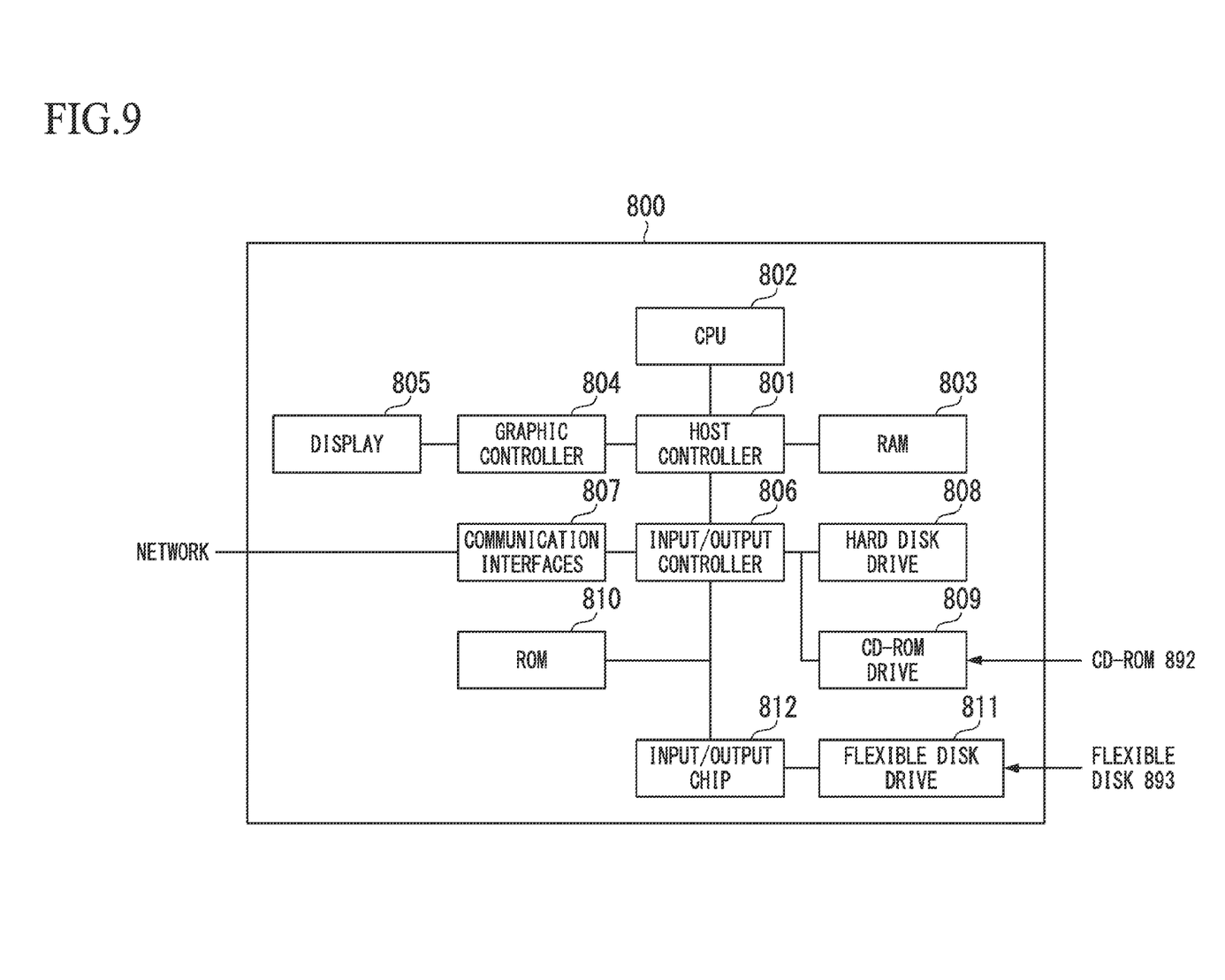
FIG. 9 is a drawing showing an example of hardware configuration of a computer 800 constituting the productivity evaluation devices 110, 210, 310 and 410 according to the present embodiment.

FIG. 9 shows an example of hardware configuration of a computer 800 constituting the productivity evaluation devices 110, 210, 310 and 410 according to the present embodiment. The computer 800 according to the present embodiment includes:

a CPU (Central Processing Unit) peripheral section including a CPU 802, a RAM (Random Access Memory) 803, a graphic controller 804, and a display 805 which are mutually connected through a host controller 801;

an input/output section including a communication interface 807, a hard disk drive 808, and a CD-ROM (Compact Disk Read Only Memory) drive 809 which are mutually connected through an input/output controller 806; and a legacy input/output section including ROM (Read Only Memory) 810, a flexible disk drive 811, and an input/output chip 812 which are connected through an input/output controller 806.

A host controller 801 connects the RAM 803, the CPU 802 which assesses the RAM 803 at a high transfer rate, and the graphic controller 804. The CPU 802 operates based on programs stored in the ROM 810 and the RAM 803, and controls each of the constituent units. The graphic controller 804 acquires graphic data generated on a frame buffer provided in the RAM 803 by the CPU 802, etc., and displays the graphic data on the display 805. Alternatively, the graphic controller 804 may contain a frame buffer storing data generated by the CPU 802, etc.

The input/output controller 806 connects the host controller 801, the communication interface 807 which is a relatively high-speed input/output device, the hard disk drive 808, and the CD-ROM (Compact Disk Read Only Memory) drive 809. The hard disk drive 808 stores a program and data used by the CPU 802 in the computer 800. From the CD-ROM drive 809, the program or the data is read and provided to the hard disk drive 808 through the RAM 803.

The input/output controller 806 is connected to the ROM 810, the flexible disk drive 811, and the input/output chip 812 which is a relatively low-speed input/output device. The ROM 810 stores a boot program executed at the time of starting up the computer 800 and/or a program depending on the hardware of the computer 800. From the flexible disk drive 811, a program or data is read and provided to the hard disk drive 808 through the RAM 803. The input/output chip 812 connects the flexible disk drive 811 to the input/output controller 806, and connects various input/output devices to the input/output controller 806 through, for example, a parallel port, a serial port, a keyboard port or a mouse port.

The program provided to the hard disk drive 808 through the RAM 803 is provided by users with being stored in a recording medium such as the flexible disk 893, the CD-ROM 892, or an IC (Integrated Circuit) card, etc. The program is read from the recording medium, installed in the hard disk drive 808 in the computer 800 through the RAM 803, and executed in the CPU 802.

The program according to the first embodiment is installed in the computer 800, and causes the computer 800 to a perform function of the productivity evaluation device 110. The program according to the first embodiment, in step S101, causes the computer 800 to perform a function of the first carbon mass calculation unit 111 which calculates the mass of carbon in the waste material. The program according to the first embodiment, in step S102, causes the computer 800 to perform a function of the second carbon mass calculation unit 112 which calculates the mass of carbon in the produced ethanol. The program according to the first embodiment, in step S103, causes the computer 800 to perform a function of the productivity evaluation unit 113 which evaluates the productivity of ethanol based on the mass of carbon calculated by the first carbon mass calculation unit and the mass of carbon calculated by the second carbon mass calculation unit.

The information processing described in this program according to the first embodiment, upon being read into the computer 800, performs functions of the first carbon mass calculation unit 111, the second carbon mass calculation unit 112, and the productivity evaluation unit 113, which are specific means realized by cooperation between the software and the various hardware components described above. By these specific means, the calculation or processing of information is realized so as to construct a specific productivity evaluation device 110 that is suited for intended use.

The program according to the second embodiment is installed in the computer 800, and causes the computer 800 to perform a function of the productivity evaluation device 210. The program according to the second embodiment, in step S201, causes the computer 800 to perform a function of the third carbon mass calculation unit which calculates the mass of carbon in the gas. The program according to the second embodiment, in step S202, causes the computer 800 to perform a function of the fourth carbon mass calculation unit which calculates the mass of carbon in the residue. The program according to the second embodiment, in step S203, causes the computer 800 to perform a function of the first carbon mass calculation unit 213 which calculates the mass of carbon in the waste material based on the mass of carbon calculated by the third carbon mass calculation unit and the mass of carbon calculated by the fourth carbon mass calculation unit. The program according to the second embodiment, in step S102, causes the computer 800 to perform a function of the second carbon mass calculation unit 112 which calculates the mass of carbon in the produced ethanol. The program according to the second embodiment, in step S103, causes the computer 800 to perform a function of the productivity evaluation unit 113 which evaluates the productivity of ethanol based on the mass of carbon calculated by the first carbon mass calculation unit and the mass of carbon calculated by the second carbon mass calculation unit.

The information processing described in this program according to the second embodiment, upon being read into the computer 800, performs functions of the third carbon mass calculation unit 211, the fourth carbon mass calculation unit 212, the first carbon mass calculation unit 213, the second carbon mass calculation unit 112, and the productivity evaluation unit 113, which are specific means realized by cooperation between the software and the various hardware components described above. By these specific means, the calculation or processing of information is realized so as to construct a specific productivity evaluation device 210 that is suited for intended purpose.

The program according to the third embodiment is installed in the computer 800, and causes the computer 800 to perform a function of the productivity evaluation device 310. The program according to the third embodiment, in step S201, causes the computer 800 to perform a function of the third carbon mass calculation unit which calculates the mass of carbon in the gas. The program according to the third embodiment, in step S202, causes the computer 800 to perform a function of the fourth carbon mass calculation unit which calculates the mass of carbon in the residue. The program according to the third embodiment, in step S301, causes the computer 800 to perform a function of the fifth carbon mass calculation unit 311 which calculates the mass of carbon in the combustion improver. The program according to the third embodiment, in step S302, causes the computer 800 to perform a function of the first carbon mass calculation unit 312 which calculates the mass of carbon in the waste material based on the mass of carbon calculated by the third carbon mass calculation unit, the mass of carbon calculated by the fourth carbon mass calculation unit, and the mass of carbon calculated by the fifth carbon mass calculation unit 311. The program according to the third embodiment, in step S102, causes the computer 800 to perform a function of the second carbon mass calculation unit 112 which calculates the mass of carbon in the produced ethanol. The program according to the third embodiment, in step S103, causes the computer 800 to perform a function of the productivity evaluation unit 113 which evaluates the productivity of ethanol based on the mass of carbon calculated by the first carbon mass calculation unit and the mass of carbon calculated by the second carbon mass calculation unit.

The information processing described in this program according to the third embodiment, upon being read into the computer 800, performs functions of the third carbon mass calculation unit 211, the fourth carbon mass calculation unit 212, the fifth carbon mass calculation unit 311, the first carbon mass calculation unit 312, the second carbon mass calculation unit 112, and the productivity evaluation unit 113, which are specific means realized by cooperation between the software and each of the various hardware components described above. By these specific means, the calculation or processing of information is realized so as to construct a specific productivity evaluation device 310 that is suited for intended purpose.

The program according to the fourth embodiment is installed in the computer 800, and causes the computer 800 to perform a function of the productivity evaluation device 410. The program according to the fourth embodiment, in step S101, causes the computer 800 to perform a function of the first carbon mass calculation unit 111 which calculates the mass of carbon in the waste material. The program according to the fourth embodiment, in step S102, causes the computer 800 to perform a function of the second carbon mass calculation unit 112 which calculates the mass of carbon in the produced ethanol. The program according to the fourth embodiment, in step S401, causes the computer 800 to perform a function of the carbon dioxide emission calculation unit 411 which calculates the amount of carbon dioxide emission caused due to the use of energy. The program according to the fourth embodiment, in step S402, causes the computer 800 to perform a function of the productivity evaluation unit 412 which evaluates the productivity of ethanol based on the mass of carbon calculated by the first carbon mass calculation unit, the mass of carbon calculated by the second carbon mass calculation, and the amount of carbon dioxide emission calculated by the carbon dioxide emission calculation unit 411.

The information processing described in this program according to the fourth embodiment, upon being read into the computer 800, performs functions of the first carbon mass calculation unit 111, the second carbon mass calculation unit 112, the carbon dioxide emission calculation unit 411, and the productivity evaluation unit 412, which are specific means realized by cooperation between the software and each of the various hardware components described above. By these specific means, the calculation or processing of information is realized so as to construct a specific productivity evaluation device 410 that is suited for intended use.

The performance of the computer 800 is explained below, taking as an example the case where the computer 800 communicates with the outer devices, etc. The CPU 802 executes the communication program loaded on the RAM 803, and instructs the communication interface 807 to execute the communication processing based on the processing content described in the communication program. The communication interface 807, being controlled by the CPU 802, reads transmission data stored in a transmission buffer area formed in the storage device, such as the RAM 803, the hard disk drive 808, the flexible disk 893, or the CD-ROM 892, and transmits the data to the network, or receives data from the network and writes the received data into a receiving buffer area formed in the storage device. Thus, the communication interface 807 may exchange the transmission/receiving data with the storage device by way of direct memory access. Alternatively, the CPU 802 may read the data from the communication interface 807 and transfer the transmission/receiving data by writing the data into the communication interface 807 as the destination or the storage device.

From files stored in the outer storage device (such as the hard disk drive 808, the CD-ROM 892, or the flexible disk 893) or database, all or a required part of data is read by the CPU 802 into RAM 803 by way of direct memory access transfer or the like, and the CPU 802 performs various sets of processing on the data in the RAM 803. The CPU 802 writes the processed data back into the outer storage device by way of direct memory access transfer or the like.

In such process, it can be regarded that the RAM 803 temporarily stores the content of the outer storage device; therefore, in the present embodiment, the RAM 803 and the outer storage device, etc. are collectively referred to as a memory, a storage unit, a storage device, etc. Various information, such as a program, a data, a table, a database and the like in the present embodiment, is stored in such a storage device as mentioned above, and becomes the object of the information processing. The CPU 802 also can store a part of the contents of RAM 803 in the cash memory, and read from and write into the cash memory. Even in such embodiment, since the cash memory serves a part of the function of RAM 803, in the present embodiment, the cash memory is also included in the RAM 803, the memory, and/or the storage device unless otherwise specified to distinguish these components.

With respect to the data read from the RAM 803, the CPU 802 performs various sets of processing, including the calculations, the processing of information, the condition determination, the search and the replacement of information, which are described in connection with the present embodiment and are specified by instruction string, and writes back the results into the RAM 803. For example, in the case of performing the condition determination, the CPU 802 determines whether the variables shown in the present embodiment satisfy conditions such as being larger or smaller than, higher or lower than, equal or not equal to, other variables or constants. Based on the results of the determination (i.e., the condition is satisfied, or not satisfied), the CPU 802 branches to a different instruction string or invoke a subroutine.

The CPU 802 can search information stored in the file in the storage device, the database or the like. For example, in the case that multiple entries where the values of the second attributes are associated with the values of the first attributes are stored in the storage device, the CPU 802 searches for an entry in which the values of the first attributes matches a specified condition from among the multiple entries stored in the storage device, and reads the values of the second attributes stored in the entry, whereby the CPU 802 can obtain the values of the second attributes associated with the first attributes satisfying the predetermined condition.

The program or module described above may be stored in the outer recording medium. Examples of usable recording medium include not only the flexible disk 893 and the CD-ROM 892, but also an optical recording medium such as DVD (Digital Versatile Disk) or CD (Compact Disk), a magneto-optical recording medium such as MO (Magneto-Optical disk), a tape media, a semiconductor memory such as an IC card. The program may be provided to the computer 800 through network by using, as a storage device, a hard disk in a server system connected to private communication network or internet, or a recording medium such as RAM.

Though the present invention is described as above using the embodiments, the technical scope of the present invention is not limited to the embodiments described above. It is obvious for a person ordinary skilled in the art that the embodiments described above can be modified or improved in various manners. It is obvious from the description of the CLAIMS that such modified or improved embodiments are also included in the technical scope of the present invention.

It should be noted that the order of execution of respective processes in operations, procedures, steps and stages or the like in the method, apparatus, program, and recording medium shown in the scope of claims, specification, and drawings is not explicitly defined, such as "before . . . " or "prior to . . . " or the like in particular, and the processes can be realized in various orders unless the output of a preceding process is used in a subsequent process. Although description is given for convenience using terms like "first" or "next" regarding an operation flow in the scope of claims, specification, and drawings, this does not imply that it is mandatory that the processes should be executed in this order.

INDUSTRIAL APPLICABILITY

According to the present invention, it is possible to efficiently evaluate the productivity of chemical substances such as ethanol in production thereof from a waste material.
110 Productivity evaluation device
111 First carbon mass calculation unit
112 Second carbon mass calculation unit
113 Productivity evaluation unit
210 Productivity evaluation device
211 Third carbon mass calculation unit
212 Fourth carbon mass calculation unit
213 First carbon mass calculation unit
310 Productivity evaluation device
311 Fifth carbon mass calculation unit
312 First carbon mass calculation unit
410 Productivity evaluation device
411 Carbon dioxide emission calculation unit
412 Productivity evaluation unit
800 Computer
801 Host controller
802 CPU
803 RAM
804 Graphic controller
805 Display
806 Input/output controller
807 Communication interfaces
808 Hard disk drive
809 CD-ROM drive
810 ROM
811 Flexible disk drive
812 Input/output chip
891 Network communication device
892 CD-ROM
893 Flexible disk

The invention claimed is:
1. A method for producing a chemical substance, comprising:

a step of obtaining a waste material that is selected from the group consisting of domestic flammable trash, a waste solid fuel, and a waste material derived from petroleum, a first carbon mass calculation stage of calculating mass of carbon contained in the waste material by multiplying a total mass of the waste material by a ratio of the mass of carbon in the waste material to the total mass of the waste material, wherein a total weight of the waste material is calculated by subtracting a weight of a garbage truck not loaded with the waste material from a weight of a garbage truck loaded with the waste material, a first step in which a material gas containing carbon monoxide and hydrogen is obtained due to thermal decomposition and chemical reaction of the waste material, a second step in which a chemical substance is synthesized from the material gas by reacting the material gas in the presence of a microbial catalyst, a second carbon mass calculation stage of calculating mass of carbon contained in the chemical substance produced in the second step.

2. The method for producing a chemical substance according to claim 1, further comprising:

a third carbon mass calculation stage of calculating mass of carbon contained in the material gas, after the first step and before the second step.

3. The method for producing a chemical substance according to claim 1, further comprising:

a carbon dioxide emission calculation stage of calculating an amount of carbon dioxide emission caused due to use of energy in the first step.

4. The method for producing a chemical substance according to claim 1, wherein the chemical substance is a compound represented by the formula $C_xH_yO_z$.

5. The method for producing a chemical substance according to claim 4, wherein the chemical substance is ethanol.

6. The method for producing a chemical substance according to claim 1, wherein the waste material is not wood chips.

7. The method for producing a chemical substance according to claim 1, wherein, in the first carbon mass calculation stage, the ratio of the mass of carbon in the waste material to the total mass of the waste material is calculated by an elemental analysis method.

8. The method for producing a chemical substance according to claim 1, which further comprises a productivity evaluation stage of evaluating the productivity of the chemical substance based on values of the mass of carbon which are calculated in the first carbon mass calculation stage and the second carbon mass calculation stage.

9. The method for producing a chemical substance according to claim 8, which further comprises a charging stage of determining a charge for the waste material depending on the productivity of the chemical substance evaluated by the productivity evaluation stage.

* * * * *